United States Patent [19]

Teagle

[11] Patent Number: 4,891,986
[45] Date of Patent: Jan. 9, 1990

[54] APPARATUS FOR INSPECTING ARTICLES

[75] Inventor: Paul Teagle, Surrey, England

[73] Assignee: British Aerospace Public Limited Company, London, England

[21] Appl. No.: 352,626

[22] Filed: May 16, 1989

Related U.S. Application Data

[63] Continuation of Ser. No. 222,285, Jul. 21, 1988, abandoned, which is a continuation of Ser. No. 65,758, Jun. 24, 1987, abandoned.

[30] Foreign Application Priority Data

Jun. 24, 1986 [GB] United Kingdom ............... 8615433
Aug. 15, 1986 [GB] United Kingdom ............... 8619911

[51] Int. Cl.$^4$ .......................................... G01N 29/04
[52] U.S. Cl. ............................... 73/634; 73/620; 324/262
[58] Field of Search ............... 73/634, 601, 618, 620, 73/633; 324/262, 73 PC; 356/378, 380, 387; 33/644, 645, 637, 634

[56] References Cited

U.S. PATENT DOCUMENTS

| | | | |
|---|---|---|---|
| 4,434,659 | 3/1984 | Kurtz et al. | 73/620 |
| 4,596,037 | 6/1986 | Bouchard et al. | 356/387 |
| 4,622,517 | 11/1986 | Arnaud et al. | 324/262 |
| 4,627,291 | 12/1986 | Otsuki et al. | 73/634 |

*Primary Examiner*—John Chapman
*Assistant Examiner*—Robert P. Bell
*Attorney, Agent, or Firm*—Cushman, Darby & Cushman

[57] ABSTRACT

An apparatus for locating the geometrical center of symmetrically shaped bore (3) in a material (2) includes a detector (4) distinguishably responsive to a property of the material (2), bore traversing means (6, 9, 10, 11) for moving the detector (4) adjacent the material (2) and along a predetermined raster scan path, and control means (15, 16, 17) responsive to changes in electrical signal outputs of the detector (4) as the traversing means (6, 9, 10 11) is scanned across the bore (3) in two mutually orthogonal directions. The control means is operative to monitor the coordinates of the interceptions of each of two mutually perpendicular chords across the bore (3) with an edge of the material (2), and to calculate the coordinates of the center of the bore (3) from these. Preferably the apparatus includes an eddy current detector (4) for determining the position of a bore (3) and an ultrasonic detector (5) for inspecting the material (2) around the bore (3) for flaws.

22 Claims, 2 Drawing Sheets

APPARATUS FOR INSPECTING ARTICLES

This is a continuation of application Ser. No. 222,285 filed July 21, 1988, which was abandoned upon the filing hereof, and which is a continuation of application Ser. No. 065,758, filed June 24, 1987, now abandoned.

BACKGROUND OF THE INVENTION

This invention relates to article inspection apparatus and in particular though not exclusively to apparatus for locating the center of a fastener in a base material of a different permeability to that of the fastener e.g., bore centering.

One area of useful application of the invention is the aircraft industry In aircraft construction it is common for stressed skins to be attached to supporting structures by fasteners located in countersunk bores in the skins. Many hundreds of such fasteners may be used regularly spaced apart with a pitch interval of 2 or 3 cms. The bores for such fasteners are potential crack propagation sites and hence require regular inspection e.g. by ultrasonic non-destructive test apparatus. Previous methods of test require removal of the fasteners before scanning for cracks with a hand held probe which is time consuming and removal of the fasteners often entails re-boring of the fastener holes because of aviation rules governing the disturbance of vital parts.

SUMMARY OF THE INVENTION

According to this invention an apparatus for locating the geometrical centre of a symmetrically shaped bore in a material includes a detector distinguishably responsive to a property of the material, bore traversing means for moving the detector adjacent the material and along a predetermined raster scan path and control means responsive to changes in electrical signal outputs of the detector as the traversing means is scanned across a bore in two mutually orthogonal directions and operative to monitor the coordinates of the interceptions of each of two mutually perpendicular scanned chords across the bore with an edge of the material, and to calculate the coordinates of the centre of the bore from these.

Preferably the control means is responsive to a first change in an electrical signal output of the detector to store data representing the coordinates of a first location of the traversing means, responsive to a second change in the electrical signal output of the detector to store data representing the coordinates of a second location of the traversing means, operative to calculate the coordinates of a point midway between the first and second locations, to drive the traversing means to the midpoint and to cause the traversing means to then move in a direction substantially orthogonal to a line joining to the first and second locations, responsive to a third change in the electrical signal output of the detector to store data representing the coordinates of a third location of the traversing means and o reverse the direction of movement of the traversing means, responsive to a fourth change in the electrical signal output of the detector to store data representing the coordinates of a fourth location of the traversing means and operative to calculate and store the coordinates of a point midway between the third and fourth locations, the midway points corresponding to the geometrical centre of the bore.

The detector may be an eddy current detector or an ultrasonic detector which both locates the position of a bore and inspects the material around the bore for flaws. Preferably, however, the apparatus includes an eddy current detector for determining the position of a bore and an ultrasonic detector for inspecting the material around the bore for flaws.

Preferably the the detector for inspecting the material for flaws is mounted on a turntable to enable it to be moved around the bore. It is also preferred that detector is responsive to differences in the properties between the base material and fasteners which are inserted in the bores to enable the bores to be detected without removal of the fasteners.

BRIEF DESCRIPTION OF THE DRAWINGS

A particular example of an apparatus in accordance with this invention will now be described with reference to the accompanying drawings, in which.

DESCRIPTION OF PREFERRED EXAMPLE

Figure 1:
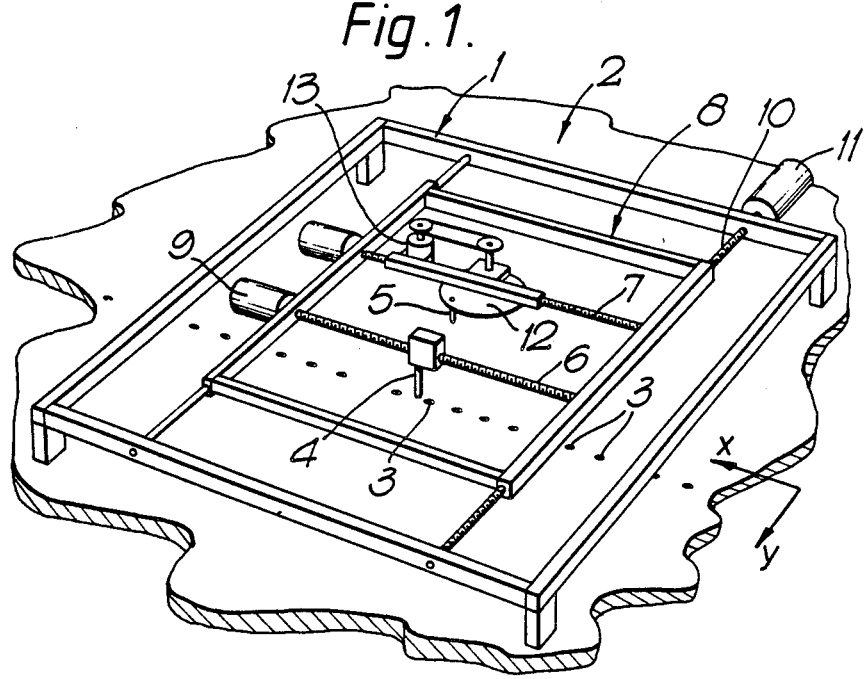
FIG. 1 is a perspective view of the apparatus.

Operation of the apparatus is now described with reference to FIG. 1. The detection apparatus comprises a rectangular framework 1 which is placed over the surface of a sheet of material 2 in the region of a fastener or bore 3. An eddy current probe 4 and ultrasonic probe 5 are mounted on shafts 6 and 7 carried by a smaller frame 8. The frame 8 is movably mounted inside the larger frame 1. Each of the probes 4 and 5 has two degrees of movement, both can move within the frame 8 along an x-axis and can move along a y axis within the large frame 1. The probe 4 is mounted on a lead screw 6 and is moved by worm gear action; lead screw 6 is driven by a motor 9. The frame 8 is also driven by worm gear action along a lead screw 10 by a motor 11. The eddy current probe 4 detects the presence of a fastener in the base material by detecting a change between the magnetic properties of the base material and the fastener. The eddy current probe scans backwards and forwards along an x axis within frame 8 and the frame 8 is moved in successive increments along the y axis until the x and y coordinates of the mid point of the fastener are found as will be described later.

When both the x and y coordinates have been found for the centre of the fastener the eddy current probe is moved off the fastener and ultrasonic flaw detection probe 5 is moved into position over the fastener. The ultrasonic probe 5 is mounted on a turntable 12 which rotates so that the probe 5 scans the periphery of the fastener along the boundary between the fastener and the sheet of base material. The turntable 12 is driven round by a motor 13 via a pulley system. Although the position locating probe is shown as being an eddy current transducer and the flaw detection probe is shown as being an ultrasonic transducer, other arrangements are possible in which the position locating and/or flaw detection probes are both ultrasonic transducers, or both eddy current transducers.

Figure 2:
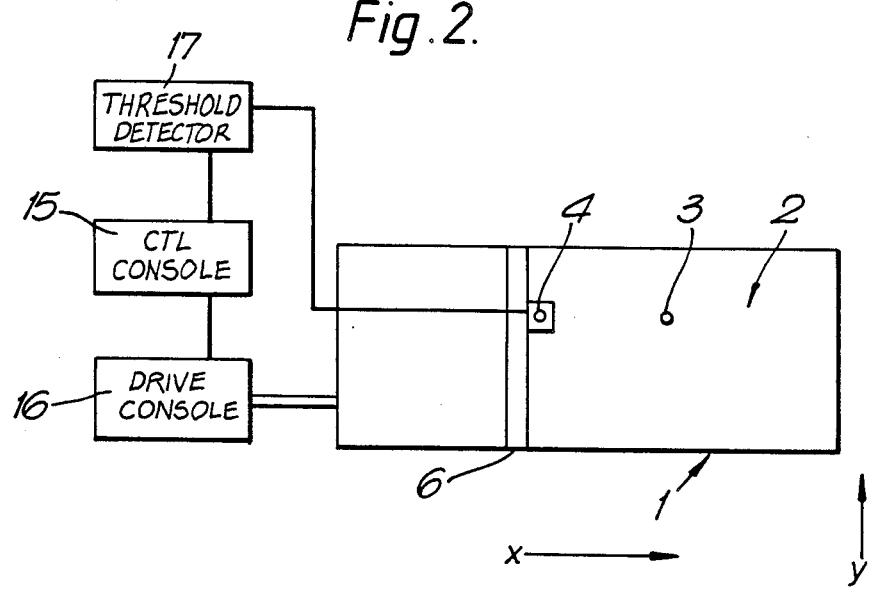
FIG. 2 is a schematic diagram of the control system.

FIG. 2 is a schematic diagram of the arrangement shown in FIG. 1 and shows the control system to comprise a control console 15 connected to a scanning frame device 1 via a drive console 16 to control the scanning repertoire of the eddy current probe 4. The signal from the probe 4 is monitored by an eddy current threshold detector 17. The eddy current threshold to which the detector 17 is responsive may be adjusted to enable the sensitivity of the eddy current probe to be increased or reduced; in this particular instance the sensitivity is reduced so that the probe is only responsive to changes at the edges of the fastener and not to different features on the head of the fastener. For instance the fasteners might have slots machined in their surface to enable them to receive a driving tool; if the eddy current probe is too sensitive it will detect the edges of the slots and confuse them with the edges of the fastener and thus give rise to an inaccurate calculation of the centre of the fastener head.

The eddy current threshold detector 17 is tuned so that the probe 4 only detects a change as it moves from one material to another i.e. for transitions from the base material to fastener (B/f) and for transitions from the fastener to base material (f/B). Initially the probe 4 is scanned across the base material 2 along the x axis within frame 8. After each scan the probe 4 is moved in the y direction by lead screw 10 by an increment which is less than half of the fastener head diameter so that the distance between successive scan lines is less than half of the fastener head diameter. The probe 4 continues scanning along the x-axis until the edge of a fastener is detected. When a fastener is detected the scanning is stopped. The probe 4 is then moved in the +y direction for one scan increment to position the probe 4 further onto the fastener. The probe is then moved in the −x direction one scan increment beyond the f/B transition.

Figure 3A:
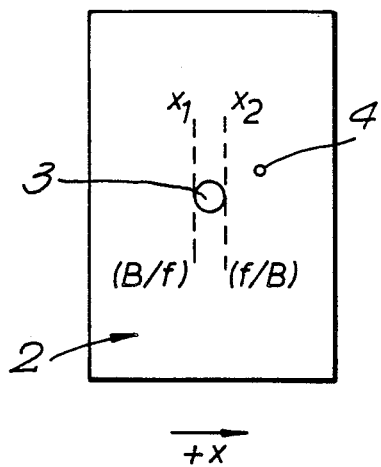
FIGS. 3a to 3b schematically represent a fastener in a panel of base material and show the x coordinates being found at the edges of a fastener; and, FIGS. 4a to 4b represent a fastener in a panel of base material and show the y coordinates being located at the edges of a fastener.
Figure 3B:
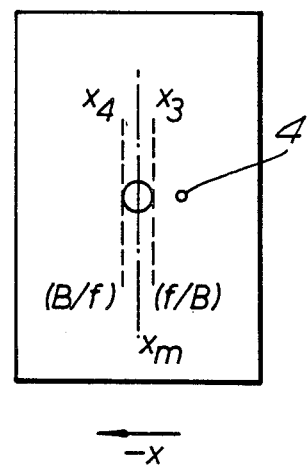
Figure 4A:
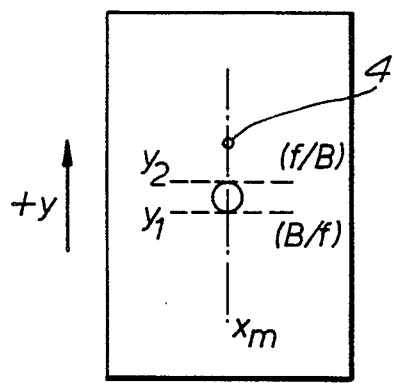

Referring to FIG. 3a the probe 4 is moved in the +x direction until the transition between the base material and fastener (B/f) is detected; this transition is then logged with a coordinate $x_1$. The probe 4 continues to scan in the +x direction until the fastener to base material (f/B) transition is detected and logged as coordinate $x_2$. The probe is then moved for one increment past the (f/B) transition in the +x direction and a mid point $m_1$ is calculated for $x_2$ and $x_1$. The direction of the scan is then reversed (FIG. 3b) and the positions of the (f/B) and (B/f) transitions are recorded with the coordinates $x_3$ and $x_4$ respectively. A midpoint $m_2$ is calculated for the coordinates $x_3$ and $x_4$. An advantage of measuring coordinates from B/f and f/B transitions in that the effects of hysteresis can be reduced when an average is taken. By sweeping the fastener in opposite directions the effects of hysteresis can be reduced and a more accurate measurement of the centre of a fastener can be produced. Finally a mean coordinate $x_m$ is calculated from $m_1$ and $m_2$ which is taken to be the x-coordinate of the centre of the fastener head. When the $x_m$ coordinate has been determined the probe is moved to the coordinate $x_m$ and the probe is scanned incrementally along the y axis along an axis which passes through $x_m$. The probe is moved in the −y direction until it detects the (f/B) transition. The probe is then moved one increment past the (f/B) transition in the −y direction. In FIG. 4a the probe 4 is moved in the +y direction until it detects the position of the (B/f) transition the coordinate $y_1$ of this transition is logged and the probe moved further along the y direction until the (f/B) transition is detected and logged as coordinate $y_2$. The probe is then moved one increment, from the (f/B) transition, in the +y direction and a mean value $m_3$ is calculated for the two coordinates $y_1$ and $y_2$.

Figure 4B:
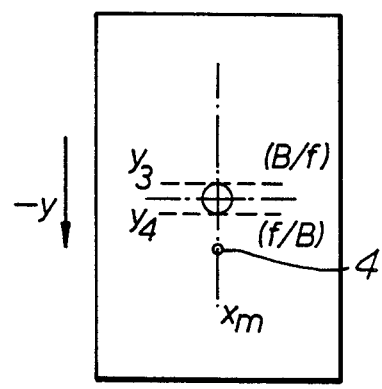

This procedure is repeated in FIG. 4b except that the probe scans in the −y direction to record the coordinates of the (B/f) and (f/B) transitions at $y_3$ and $y_4$. A mean value of $m_3$ and $m_4$ is then calculated to give a mean value $y_m$ of the y coordinate which is taken to be the y coordinate of the centre of the fastener head. The fastener bore centre is then given by the coordinates $x_m$ and $y_m$. The number of scans and measurements made to calculate $x_m$ and $y_m$ can be increased to improve the accuracy of finding the bore centre of the fastener.

When the centre of the fastener has been found the ultrasonic flaw detection probe, 5 in FIG. 1, is moved to the centre of the fastener to scan the fastener around the periphery using conventional ultrasonic techniques. A jet of water (not shown) is used to improve the propagation of ultrasound between the probe 5 and the material 2 being tested.

Although only one sequence of scanning movements has been described it is possible to program the probe to scan in different sequences to suit the shape of fastener or bore, for instance referring to FIGS. 3a to 4b the eddy current probe could be programmed to move along the x axis in the +x direction until it detects a difference in materials at x, (FIG. 3a) the probe could then be moved along the y axis until two y coordinates have been found (FIG. 4a). When the two y coordinates have been found their midpoint is calculated and the probe 5 is moved to that midpoint. The probe then scans in a direction substantially perpendicular to the y axis to locate the x coordinates of the edges of the bore or fastener. The geometrical centre is then calculated as the midpoint of the two x coordinates. Although the probe is shown as approaching the bore or fastener from the left hand side it could just as well be programmed to approach from the right, from above or from any other direction, without departing from the scope of the invention.

I claim:

1. Apparatus for locating the geometrical center of a symmetrically shaped bore in a material comprising:

detector means, distinguishably responsive to a property of said material for providing a signal output indicative of said property;

bore traversing means, on which said detector means is mounted, for moving said detector means adjacent said material along a raster scan path; and first means, operatively connected to said detector means and to said bore traversing means, and responsive to changes in said signal output of said detector means as said bore traversing means is scanned across a bore in two mutually orthogonal directions, for determining a position of said bore by detecting edges of said material and determining coordinates of two mutually perpendicular scanned chords across said bore and calculating coordinates of the center of said bore from said coordinates of said chords.

2. The apparatus of claim 1, wherein said bore traversing means follows said raster scan path during a search mode, and until said first means detects said edge, said first means controlling said bore traversing means to cause said bore to be scanned in said two mutually orthogonal directions in response to said edge being detected.

3. The apparatus of claim 1, wherein said detector means is at least one device selected from a group of devices consisting of an eddy current detector and an ultrasonic detector, and wherein said detector means both locates said geometrical center of said bore and also inspects said material around said bore for flaws.

4. The apparatus of claim 1, wherein said detector means comprises an eddy current detector for determining said geometrical centre of said bore and an ultrasonic detector for inspecting said material around said bore for flaws.

5. The apparatus of claim 4, wherein said bore traversing means includes a turntable, and wherein said ultrasonic detector for inspecting said material for flaws is mounted on said turntable to enable it to be moved around said bore.

6. The apparatus of claim 1, wherein said detector means is responsive to differences in the properties between said base material and a fastener inserted in said bore, to enable said bore to be detected without removal of said fasteners.

7. The apparatus of claim 1, wherein said bore traversing means includes a small frame, and a large frame, said small frame being movable mounted inside said large frame, and said detector means being movably mounted inside said small frame.

8. The apparatus of claim 7, wherein said bore traversing means also includes a first lead screw, said first lead screw being connected to and acting between said detector means and said small frame, a first motor driving said first lead screw, a second lead screw, said second lead screw being connected to and acting between said small and said large frame, and a second motor driving said second lead screw.

9. Apparatus for locating the geometrical center of a symmetrically shaped bore in a material comprising:
   detector means distinguishably responsive to a property of said material for providing a signal output indicative of said property;
   bore traversing means, on which said detector means is mounted for moving said detector means adjacent said material and along a predetermined raster scan path during a search mode; and
   first means, operatively connected to said detector means and to said bore traversing means, for:
   (1) responsive to a first change in said signal output by said detector means, storing data representing coordinates of a first location of said traversing means,
   (2) responsive to a second change in said electrical signal output by said detector means, storing data representing coordinates of a second location of said traversing means,
   (3) calculating coordinates of a first midpoint midway between said first and said second locations and ending said search mode,
   (4) driving said traversing means to said first midpoint,
   (5) subsequently driving said traversing means to then move in a direction substantially orthogonal to a line joining said first and said second locations,
   (6) responsive to third change in said electrical signal output by said detector means, storing data representing coordinates of third location of said traversing means,
   (7) then reversing a direction of movement of said traversing means,
   (8) responsive to a fourth change in said signal output of said detector means to store data representing coordinates of a fourth location of said traversing means, and
   (9) calculating and storing the coordinates of a second midpoint midway between said third and fourth locations, said first and second midpoints corresponding to the geometrical centre of said bore.

10. The apparatus of claim 9, wherein said detector means is at least one device selected from a group of devices consisting of an eddy current detector and an ultrasonic detector, and wherein said detector means both locates said geometrical center of said bore and also inspects said material around said bore for flaws.

11. The apparatus of claim 9, wherein said detector means comprises an eddy current detector for determining said geometrical centre of said bore and an ultrasonic detector for inspecting said material around said bore for flaws.

12. The apparatus of claim 11, wherein said bore traversing means includes a turntable, and wherein said ultrasonic detector for inspecting said material for flaws is mounted on said turntable to enable it to be moved around said bore.

13. The apparatus of claim 9, wherein said detector means is responsive to differences in the properties between said base material and a fastener inserted in said bore to enable said bore to be detected without removal of said fasteners.

14. The apparatus of claim 9, wherein said bore traversing means also includes a small frame, and a large frame, said small frame being movable mounted inside said large frame, and said detector means being movably mounted inside said small frame.

15. The apparatus of claim 14, wherein said bore traversing means includes a first lead screw, said first lead screw being connected to and acting between said detector means and said small frame, a first motor driving said first lead screw, a second lead screw, said second lead screw being connected to and acting between said small and said large frame, and a second motor driving said second lead screw.

16. Apparatus for locating the geometrical center of a symmetrically shaped bore in a material comprising:
   detector means distinguishably responsive to a property of said material for providing a signal output indicative of said property;
   bore traversing means, on which said detector means is mounted for moving said detector means adjacent said material along a predetermined raster scan path in a search mode; and
   first means, operatively connected to said detector means and to said bore traversing means, for:
   (1) during said traversing means moving in one direction being responsive to a first change in said electrical signal output of said detector means, for storing data representing coordinates of a first location of said traversing means at which said first change is detected,
   (2) responsive to a second change in said electrical signal output of said detector means to store data representing coordinates of a second location of said traversing means at which said second change is detected,
   (3) calculating and storing coordinates of a first midpoint midway between said first and said second locations,
   (4) then, during said traversing means moving in a direction opposite to said one direction, responsive to a third change in said signal output of said detector means to store data representing coordinates of a third location, (5) responsive to a fourth change in said signal output of said detector means while said traversing means is moving in said direction opposite to store data representing coordinates of a fourth location of said traversing means, (6) calculating and storing coordinates of a second midpoint midway between said third and said fourth locations, (7) calculating and storing an average of said first and second midpoints, (8) ending said search mode and causing said traversing means to move in a direction substantially orthogonal to said one direction, (9) responsive to a fifth change in said electrical signal output of said detector means to store data representing coordinates of a fifth location of said traversing means.

(10) then reversing said orthogonal direction of movement of said traversing means,

(11) responsive to a sixth change in said electrical signal output of said detector means to store data representing coordinates of a sixth location of said traversing means,

(12) calculating and storing coordinates of a third midpoint midway between said fifth and said sixth locations,

(13) then causing said traversing means to reverse said direction of movement,

(14) responsive to a seventh change of said electrical signal output of said detector means to store data representing coordinates of a seventh location of said traversing means,

(15) responsive to an eighth change in said electrical signal output of said detector means to store data representing coordinates of an eighth location of said traversing means

(16) calculating and storing coordinates of a fourth midpoint midway between said seventh and said eighth locations, and

(17) calculating an average of said third and fourth calculated midpoints, said calculated average midpoints corresponding to the geometrical center of said bore.

17. The apparatus of claim 16, wherein said detector means is at least one device selected from a group of devices consisting of an eddy current detector and an ultrasonic detector, and wherein said detector means both locates said geometrical center of said bore and also inspects said material around said bore for flaws.

18. The apparatus of claim 16, wherein said detector means comprises an eddy current detector for determining said geometrical centre of said bore and an ultrasonic detector for inspecting said material around said bore for flaws.

19. The apparatus of claim 18, wherein said bore traversing means includes a turntable, and wherein said ultrasonic detector for inspecting said material for flaws is mounted on said turntable to enable it to be moved around said bore.

20. The apparatus of claim 16, wherein said detector means is responsive to differences in the properties between said base material and a fastener inserted in said bore to enable said bore to be detected without removal of said fasteners.

21. The apparatus of claim 16, wherein said bore traversing means includes a small frame, and a large frame, said small frame being movable mounted inside said large frame, and said detector means being movably mounted inside said small frame.

22. The apparatus of claim 21, wherein said bore traversing means also includes a first lead screw, said first lead screw being connected to and acting between said detector means and said small frame, a first motor driving said first lead screw, a second lead screw, said second lead screw being connected to and acting between said small and said large frame, and a second motor driving said second lead screw.

* * * * *